United States Patent
Imai et al.

(10) Patent No.: US 10,317,258 B2
(45) Date of Patent: Jun. 11, 2019

(54) ROTARY ENCODER HAVING FUNCTION TO OBTAIN MOISTURE ABSORBING AMOUNT OF DESICCANT

(71) Applicant: FANUC CORPORATION, Minamitsuru-gun, Yamanashi (JP)

(72) Inventors: Keisuke Imai, Yamanashi (JP); Hirosato Yoshida, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 0 days.

(21) Appl. No.: 15/195,085

(22) Filed: Jun. 28, 2016

(65) Prior Publication Data

US 2017/0003251 A1  Jan. 5, 2017

(30) Foreign Application Priority Data

Jun. 30, 2015  (JP) ................................ 2015-131520

(51) Int. Cl.
| | |
|---|---|
| G01N 27/04 | (2006.01) |
| G01D 11/26 | (2006.01) |
| G01N 27/22 | (2006.01) |
| G01D 11/24 | (2006.01) |

(52) U.S. Cl.
CPC ........... *G01D 11/26* (2013.01); *G01D 11/245* (2013.01); *G01N 27/048* (2013.01); *G01N 27/225* (2013.01)

(58) Field of Classification Search
CPC ..... G01D 11/26; G01D 5/3473; G01N 27/225
See application file for complete search history.

(56) References Cited

U.S. PATENT DOCUMENTS

| | | | |
|---|---|---|---|
| 4,272,986 A | 6/1981 | Lowry et al. | |
| 5,968,386 A * | 10/1999 | Goenka | H05K 3/284 |
| | | | 219/209 |
| 2006/0278965 A1* | 12/2006 | Foust | H01L 51/524 |
| | | | 257/678 |
| 2011/0094115 A1* | 4/2011 | Schroter | G01D 3/022 |
| | | | 33/1 PT |
| 2012/0234078 A1 | 9/2012 | Hagl | |
| 2013/0336842 A1 | 12/2013 | Grange | |
| 2016/0161431 A1* | 6/2016 | Stagg | G01N 27/121 |
| | | | 324/694 |

FOREIGN PATENT DOCUMENTS

| | | |
|---|---|---|
| JP | 49067676 A | 7/1974 |
| JP | 61217744 A | 9/1986 |

(Continued)

OTHER PUBLICATIONS

Japanese Office Action with English language translation for Application No. 2015-131520, dated May 31, 2017, 8 pages.

*Primary Examiner* — Jermele M Hollington
*Assistant Examiner* — Feba Pothen
(74) *Attorney, Agent, or Firm* — RatnerPrestia

(57) ABSTRACT

A rotary encoder of the present invention has a hermetically sealed structure having at least one desiccant and an electric circuit by which the moisture absorbing amount of the desiccant can be obtained. The desiccant is arranged in a sealed space defined by a flange and a cover member. The electric circuit, a rotary slit plate, a light emitting element and a light receiving element are arranged in the sealed space.

6 Claims, 7 Drawing Sheets

(56) References Cited

FOREIGN PATENT DOCUMENTS

| | | |
|---|---|---|
| JP | 03076115 U | 7/1991 |
| JP | 05010911 A | 1/1993 |
| JP | H05-040104 A | 2/1993 |
| JP | 5157580 A | 6/1993 |
| JP | 07159005 A | 6/1995 |
| JP | H11-002616 A | 1/1996 |
| JP | 2001012635 A | 1/2001 |
| JP | 2001179479 A | 7/2001 |
| JP | 2002005866 A | 1/2002 |
| JP | 2002325395 A | 11/2002 |
| JP | 2005-148035 A | 6/2005 |
| JP | 2005-338764 A | 12/2005 |
| JP | 2009018970 A | 1/2009 |
| JP | 2014031913 A | 2/2014 |
| JP | 2014507003 A | 3/2014 |

* cited by examiner

ROTARY ENCODER HAVING FUNCTION TO OBTAIN MOISTURE ABSORBING AMOUNT OF DESICCANT

BACKGROUND OF THE INVENTION

1. Field of the Invention

The present invention relates to a rotary encoder having an airtight structure, and more specifically, it relates to a rotary encoder having a desiccant which is arranged in a hermetically sealed encoder body together with other components.

2. Description of the Related Art

In general, in hermetically sealed devices, condensation may occur in the devices due to a temperature difference between the external air of the devices and the internal air of the devices or water intruding into the devices. In view of this, conventionally, it is known to provide a desiccant in the devices for the purpose of absorbing the moisture entering the devices or preventing the occurrence of condensation in the devices (e.g., Japanese Patent Application Laid-open No. 2005-338764 or No. 2005-148035).

In particular, in a rotary encoder disclosed in Japanese Patent Application Laid-open No. 2005-148035, the encoder main body is hermetically sealed by a cover member but liquid can intrude into the encoder main body through a gap between a rotating axis portion of a rotary slit plate and a bearing portion supporting the rotating axis portion. Therefore, it is necessary to arrange a desiccant therein which is effective against the intruded liquid.

Moreover, it is possible to separately provide a moisture sensor or a condensation sensor in order to detect condensation. Japanese Patent Application Laid-open No. H11-2616 discloses a moisture sensor which detects the moisture and Japanese Patent Application Laid-open No. H05-40104 discloses a condensation sensor which detects condensation.

In the case where a rotary encoder is attached to, for example, a motor (servo motor) of an NC machining tool. However, the temperature and moisture in the encoder main body remarkably change due to heat of the motor or the encoder main body is exposed to liquid, e.g., cutting liquid, which tends to enter a clearance. If a sudden change in the temperature or moisture occurs or the cutting liquid enters into the encoder main body, even if a desiccant is provided in the hermetically sealed encoder main body as in the aforementioned prior art, the desiccant may not be able to absorb the liquid completely. In such cases, the encoder may be damaged by a large amount of liquid exceeding the moisture absorbing capacity of the desiccant.

SUMMARY OF THE INVENTION

The present invention provides an encoder which can obtain the moisture absorbing amount of the desiccant arranged in the hermetically sealed encoder main body to thereby prevent damage from occurring due to condensation in the encoder main body or liquid entering thereinto.

According to a first aspect of the present invention, there is provided a rotary encoder having a hermetically sealed structure, comprising at least one desiccant arranged in the rotary encoder, and an electric circuit which is configured to obtain a moisture absorbing amount of the desiccant.

According to a second aspect of the present invention, there is provided a rotary encoder according to the first aspect, further comprising a flange which is to be brought into contact with a motor, and at least one additional desiccant is arranged on the portion of the flange that is to be opposed to the motor, wherein the electric circuit is configured to obtain the moisture absorbing amount of the additional desiccant.

According to a third aspect of the present invention, there is provided a rotary encoder according to the first aspect, further comprising a flange which is to be brought into contact with a motor and a cover member which is attached to the flange and which defines a sealed space in the rotary encoder, wherein the at least one desiccant is arranged in contact with the cover member in the sealed space.

According to a fourth aspect of the present invention, there is provided a rotary encoder according to any one of the first to third aspects, wherein the electric circuit comprises a measuring unit which measures an electrical resistance of each of the desiccants, and a moisture absorbing amount calculation unit which calculates the moisture absorbing amount of each desiccant, based on the measured electrical resistance.

According to a fifth aspect of the present invention, there is provided a rotary encoder according to any one of the first to third aspects, wherein the electric circuit comprises a measuring unit which measures an electrostatic capacity of each of the desiccants, and a moisture absorbing amount calculation unit which calculates the moisture absorbing amount of each desiccant, based on the measured electrostatic capacity.

According to a sixth aspect of the present invention, there is provided a rotary encoder according to the fourth or fifth aspect, wherein the electric circuit further comprises a comparison judgment unit which judges whether or not the moisture absorbing amount calculated by the moisture absorbing amount calculation unit exceeds a predetermined threshold, and an output unit which outputs a signal to notify that each desiccant will be no longer able to absorb liquid if the calculated moisture absorbing amount exceeds the predetermined threshold.

The aforementioned object, features and merits and other objects, features and merits of the present invention will become more apparent from the description of the representative embodiments of the present invention illustrated in the accompanying drawings.

DETAILED DESCRIPTION

Figure 1:
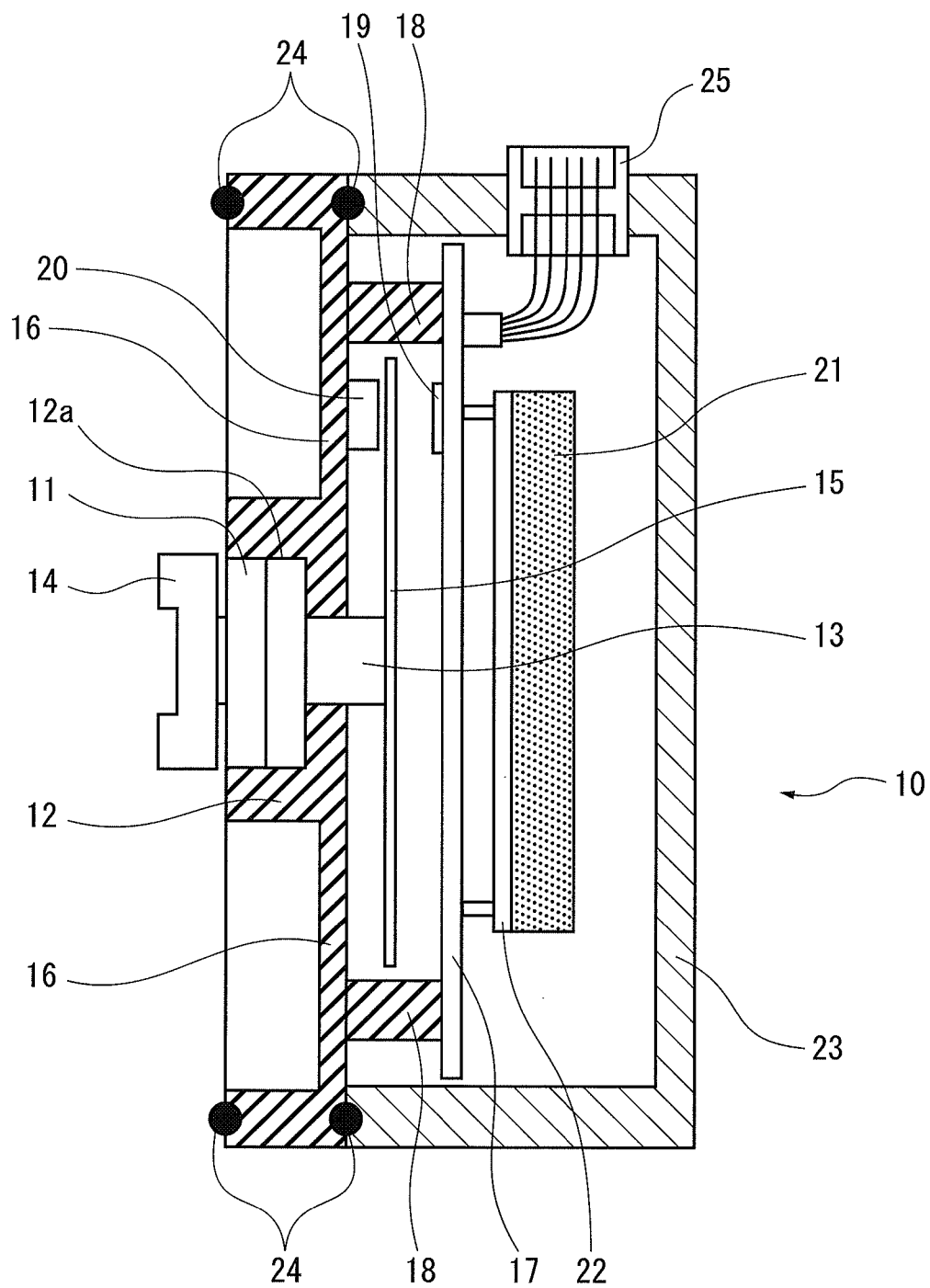
FIG. 1 is a schematic longitudinal sectional view of a rotary encoder according to a first embodiment of the present invention.

The embodiments of the invention will be discussed below with reference to the accompanying drawings. In the following discussion, the same or corresponding components are assigned the same reference numerals. For the sake of clarity, the scale of the drawings has been appropriately changed. Note that, the illustrated embodiments are merely examples for carrying out the invention and the invention is not limited to the illustrated embodiments.

First Embodiment

FIG. 1 schematically shows a longitudinal sectional view of a rotary encoder according to the first embodiment. With reference to FIG. 1, the rotary encoder 10 of the present embodiment is composed of a bearing portion 11 and a base member 12 having a hole 12a in which the bearing portion 11 is fitted. A rotating axis portion 13 extends through the bearing portion 11. The rotating axis portion 13 is provided on one of its ends, with a joint 14 which is connected to a drive axis of a motor (not shown) and, on the other end, with a rotary slit plate 15 connected thereto. The rotary slit plate 15 is provided with a plurality of slits consisting of transparent portions and nontransparent portions (not shown), arranged in the circumferential direction. The rotary slit plate 15 may be referred to as a coded plate.

The base member 12 is provided with a flange 16. An electric circuit 17 composed of a printed circuit board having electronic elements mounted thereon is arranged on the side of the rotary slit plate 15 opposite to the base member 12. The printed circuit board of the electric circuit 17 is supported on and secured to a support portion 18 provided on the flange 16 so as to provide a spatial gap between the electric circuit 17 and the base member 12. A light emitting element 19 is provided on the electric circuit 17 to be opposed to the slits of the rotary slit plate 15. A light receiving element 20 is provided on the base member 12 to be opposed to the slits of the rotary slit plate 15.

A holding member 22 which holds at least one desiccant 21 to absorb liquid is detachably attached to the printed circuit board of the electric circuit 17. A cover member 23 is detachably attached to the flange 16. The cover member 23 is shaped so as to cover all of the rotary slit plate 15, the electric circuit 17, the support portion 18, the light emitting element 19, the light receiving element 20, the desiccant 21, and the holding member 22. In order to maintain the seal of the airtight space defined by the cover member 23 and the flange 16, sealing members 24 such as an O-ring are arranged at the connecting surfaces of the cover member 23 and the flange 16. Consequently, the rotary encoder 10 is hermetically sealed. The cover member 23 is provided with an electrical connector 25 through which signals are inputted to or outputted from the electric circuit 17.

Note that, in FIG. 1, the electric circuit 17 is arranged in the airtight space in the cover member 23, but may be embedded in the cover member 23 or detachably mounted on the outer surface of the cover member 23.

Furthermore, the electric circuit 17 has a function to obtain the moisture absorbing amount of the desiccant 21. One electric circuit 17 may be provided for one desiccant 21 or two or more electric circuits 17 may be provided for one desiccant 21 to enhance accuracy of detection of the moisture absorbing amount. Furthermore, in order to acquire the moisture absorbing amount of the desiccant 21, the electric circuit 17 is provided with a means for measuring the electric characteristics such as electric resistance or electrostatic capacity or electric current and a means for calculating the moisture absorbing amount of the desiccant 21 based on the measured values of the electric characteristics. In the calculation of the moisture absorbing amount, if the relative function between the moisture absorbing amount of the desiccant 21 and the electric characteristics varies in accordance with the temperature, it is preferable that a thermometer be provided on the inner surface of the cover member 23 or on the printed circuit board of the electric circuit 17 to measure the temperature. Electrodes (not shown) are arranged at both ends of the desiccant 21 so as to apply voltage to the desiccant 21.

A cellulose derivative polymer such as polyacrylamide, polyvinyl alcohol, polyethylene oxide, methyl cellulose, or ethyl cellulose, a polyamide resin such as nylon (registered trademark), polymer such as polyvinylpyrrolidone, moisture absorbing acrylate, condensation polymer of isobutylene and maleic anhydride, or moisture absorbing methacrylate, or a moisture absorbing polymer electrolyte, such as sodium polyacrylate can be used as the desiccant 21. Alternatively, a modified substance, a composite, or a mixture of these materials may be used or carbon fibers or metal particles may be added to such a polymer as an electrolyte or electrically conductive particles.

As a function to acquire the moisture absorbing amount of the desiccant 21, it is preferable that not only a function to calculate the absolute moisture absorbing amount from absolute values (e.g., measured electric resistance or electrostatic capacity, etc. of the desiccant 21) but also a function to comprehensively calculate the moisture absorbing amount based on a change in temperature or on a relative change of the values with time be provided. In addition thereto, it is preferable to provide a function to detect the occurrence of condensation and intrusion of liquid and a function to predict the possible occurrence of damage to the rotary encoder 10 due to the condensation or intrusion of liquid, etc., from a change in the calculated values obtained by carrying out the aforementioned calculation at constant time intervals.

Moreover, the electric circuit is preferably provided with a function to predict the service life of the desiccant 21 from a non-absorbing state in which no liquid has been absorbed to a full absorption state in which a liquid has been fully absorbed and further liquid can be no longer absorbed, based on a change in the calculated moisture absorbing amount. Moreover, it may be possible for the electric circuit to have a function to output a signal corresponding to an alarm to notify that the motor should be stopped or a warning to urge maintenance in advance, based on the aforementioned prediction before the rotary encoder 10 is damaged by the condensation or an intrusion of liquid.

The electric circuit having the aforementioned functions will be discussed below in more detail.

Figure 2:
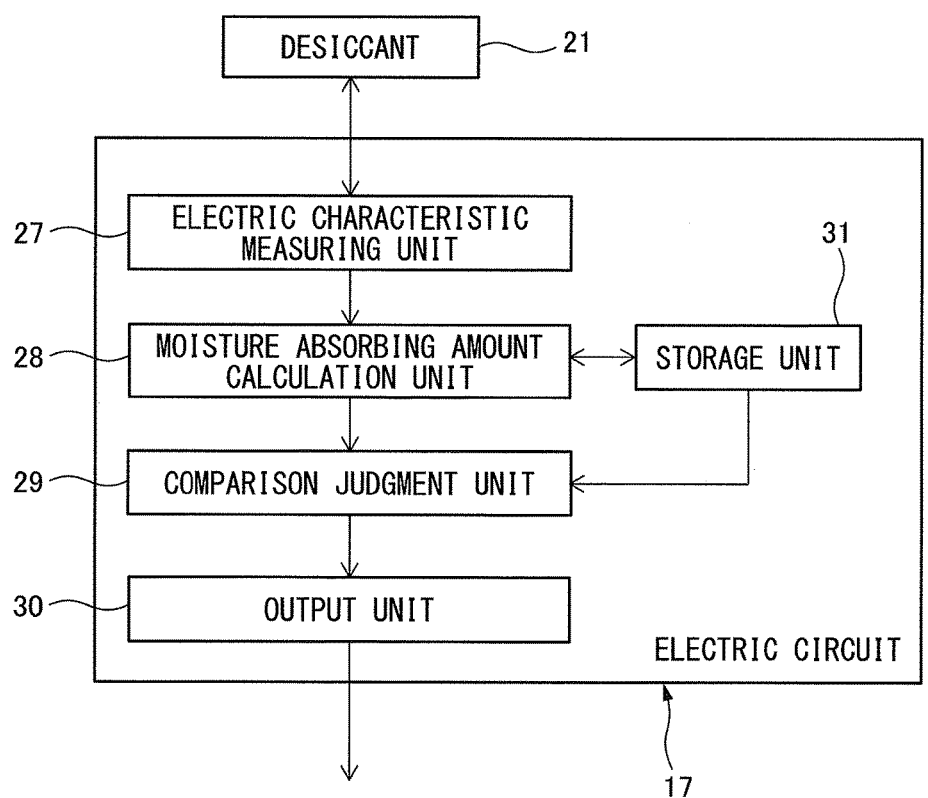
FIG. 2 is a block diagram of the structure of an electric circuit shown in FIG. 1.

FIG. 2 is a block diagram showing the structure of the electric circuit 17 shown in FIG. 1.

The electric circuit 17 illustrated in FIG. 2 is composed of an electric characteristic measuring unit 27 which measures the electric characteristics of the desiccant 21 at constant time intervals, a moisture absorbing amount calculation unit 28 which calculates the moisture absorbing amount based on the electric characteristics measured by the electric characteristic measuring unit 27, a comparison judgment unit 29 which compares the moisture absorbing amount calculated by the moisture absorbing amount calculation unit 28 with a predetermined threshold and judges whether or not the moisture absorbing amount of the desiccant 21 exceeds the predetermined threshold, and an output unit 30 which outputs a signal for sending an alarm or warning to notify that the desiccant 21 cannot absorb a further amount of liquid when the calculated moisture absorbing amount exceeds the predetermined threshold.

With the electric circuit 17 constructed as above, it is possible to detect the state in which the desiccant 21 has already absorbed an amount of liquid close to the upper limit of the absorbing capacity by appropriately setting the threshold in accordance with the absorbing capacity of the desiccant 21. As a result, it is possible to issue an alarm or warning to the outside of the rotary encoder 10 before the amount of liquid which has entered or increased due to condensation exceeds the absorbing capacity of the desiccant 21. Accordingly, damage to the rotary encoder 10 caused by the liquid can be prevented from occurring.

Furthermore, as the moisture absorbing amount of the desiccant 21 can be acquired by the electric circuit 17 provided in the rotary encoder 10 itself, it is not necessary to provide a separate moisture sensor, etc. Consequently, the rotary encoder 10 can be miniaturized and the manufacturing cost can be reduced.

Furthermore, it is preferable that the electric circuit 17, as shown in FIG. 2, be provided with a storage unit 31 which successively stores the moisture absorbing amounts calculated by the moisture absorbing amount calculation unit 28. If such a storage unit 31 is provided, the comparison judgment unit 29 can compare the calculated moisture absorbing amount and the moisture absorbing amount stored in the storage unit 31 just before the comparison each time the moisture absorbing amount is calculated by the moisture absorbing amount calculation unit 28. If there is a sudden increase of the change in the moisture absorbing amount, it is preferable that the comparison judgment unit 29 judge that the amount of liquid which has been increased owing to intrusion or condensation may exceed the absorbing capacity of the desiccant 21 and instruct the output unit 30 to send an alarm or warning signal to the outside of the rotary encoder 10.

As the storage unit 31 in which the calculated moisture absorbing amounts are successively stored is provided, it is possible to calculate a change rate of the moisture absorbing amount with time based on the plurality of moisture absorbing amounts which have been successively stored and the time which has elapsed from the commencement of the measurement of the electrical characteristics of the desiccant 21. An approximate period of time from the non-absorbing state of the desiccant 21 to the full absorption state thereof can be obtained by dividing the maximum liquid absorption amount of the desiccant 21 which has been obtained beforehand by the change rate of the moisture absorbing amount with time. With the calculation of such a period of time by the moisture absorbing amount calculation unit 28, the comparison judgment unit 29 can instruct the output unit 30 to issue an alarm or warning signal to the outside of the rotary encoder 10 before the desiccant 21 becomes disabled. Namely, it is possible to urge maintenance before the rotary encoders fails by predicting the time from the commencement of the use of the rotary encoder 10 to the occurrence of the failure.

The preferred embodiments of the circuit for the electrical characteristic measuring unit 27 will be discussed below.

It is necessary for the electric characteristic measuring unit 27 to measure the electric characteristics of the desiccant 21, for example, the electric resistance, the electrostatic capacity, or the electric current, etc., in order to calculate the moisture absorbing amount of the desiccant 21.

Figure 3:
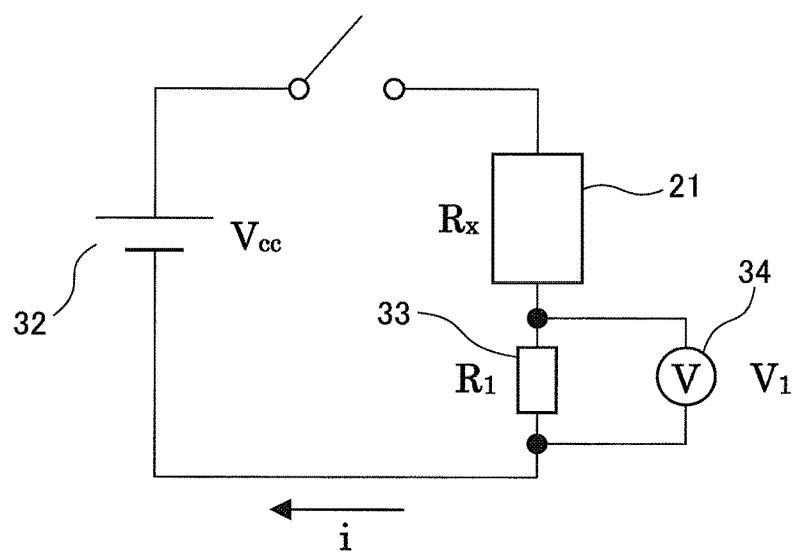
FIG. 3 is a circuitry diagram of a circuit for measuring the electric resistance of the desiccant.

FIG. 3 shows a circuitry for measuring the electric resistance of the desiccant 21 by way of example. In FIG. 3, it is assumed that the voltage of the power source 32 is Vcc, the electric resistance of the desiccant 21 is Rx, and the fixed resistance of the fixed resistor 33 is R1. The power source 32, the desiccant 21, and the fixed resistor 33 are connected in series, and the voltage measuring circuit 34 which measures the voltage V1 applied to the fixed resistor 33 is connected to the fixed resistor 33 in parallel.

In this circuitry, the current i flowing through the whole circuit is measured from the voltage V1 applied to the fixed resistor 33 using the following equation (1).

$$i = V1/R1 \qquad (1)$$

As can be seen in equation (2) below, the electric resistance Rx of the desiccant 21 can be obtained from the current i, voltage V1, and power source voltage Vcc.

$$Rx = (Vcc - V1)/i \qquad (2)$$

Figure 4:
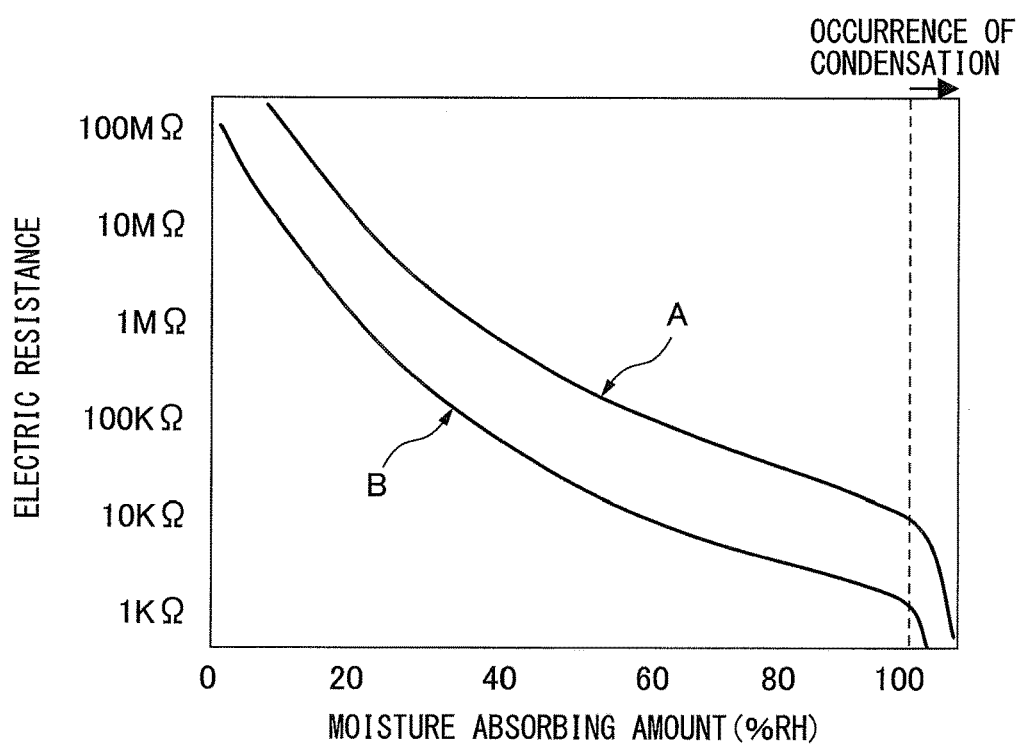
FIG. 4 is a graph showing the relationship between the moisture absorbing amount and the electric resistance.

Moreover, FIG. 4 is a graph showing a relationship between the moisture absorbing amount and the electric resistance. In FIG. 4, the curve A represents the case when the temperature is 25° C. and the curve B represents the case when the temperature is 60° C.

As may be understood from FIG. 4, the larger the moisture absorbing amount of the desiccant 21, the larger the amount of ions ionized by the moisture, and accordingly, the smaller the electric resistance of the desiccant 21. Furthermore, the higher the temperature, the larger the absolute moisture amount in the air, and accordingly, the electric resistance decreases as the temperature increases for the same moisture absorbing amount. As mentioned above, there is a correlation between the electrical resistance of the desiccant 21 and the moisture absorbing amount of the desiccant 21, and the curve which represents the correlation between the moisture absorbing amount and the electrical resistance is shifted upward or downward depending on the temperature. Therefore, by measuring the electrical resistance of the desiccant 21 by the circuit shown in FIG. 3 and measuring the ambient temperature of the desiccant 21, it is possible to obtain the moisture absorbing amount of the desiccant 21 based on the correlation between the moisture absorbing amount and the electrical resistance as shown in FIG. 4. In this case, for example, it is preferable that correlative function between the moisture absorbing amount and the electrical resistance, including the temperature as a correction coefficient be obtained beforehand by experiments or simulation, etc., and be stored in the moisture absorbing amount calculation unit 28 shown in FIG. 2.

Figure 5A:
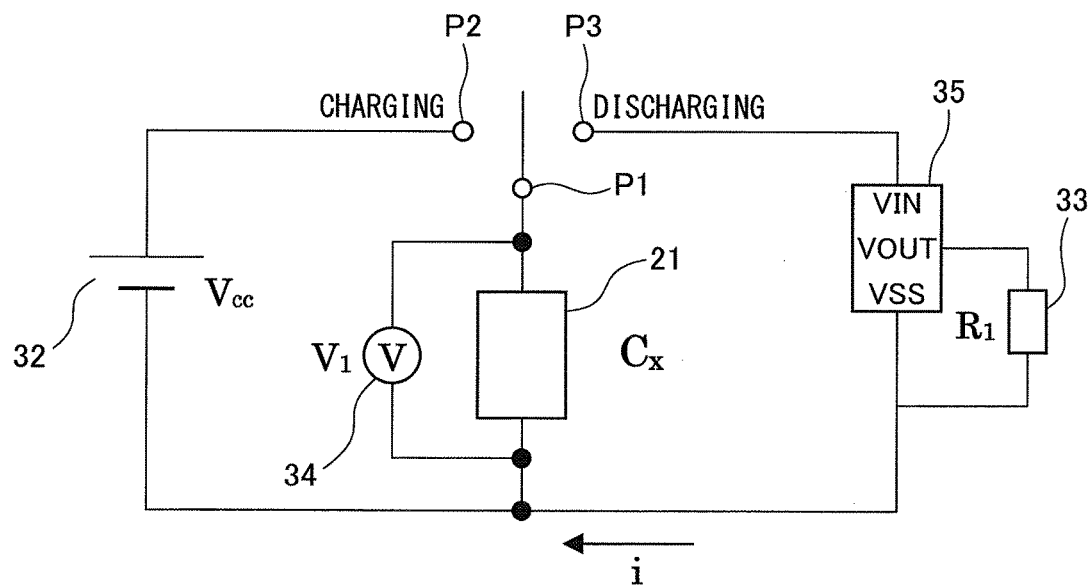
FIG. 5A is a circuitry diagram of a circuit for measuring the electrostatic capacity of the desiccant by way of example.

FIG. 5A illustrates an example of a circuit for measuring the electrostatic capacity of the desiccant 21.

In FIG. 5A, it is assumed that the voltage of the power source 32 is Vcc, the electrostatic capacity of the desiccant 21 is Cx, and the fixed resistance of the fixed resistor 33 is R1. The power source 32 and the desiccant 21 are connected in series, and the voltage measuring circuit 34 which measures the voltage V1 applied to the desiccant 21 is connected to the desiccant 21 in parallel to form a charging circuit for the desiccant 21. Furthermore, the desiccant to which the voltage measuring circuit 34 is connected in parallel and the fixed resistor 33 are connected in series through a three-terminal regulator 35 to form a discharging circuit for discharging the charged current of the desiccant 21.

Figure 5B:
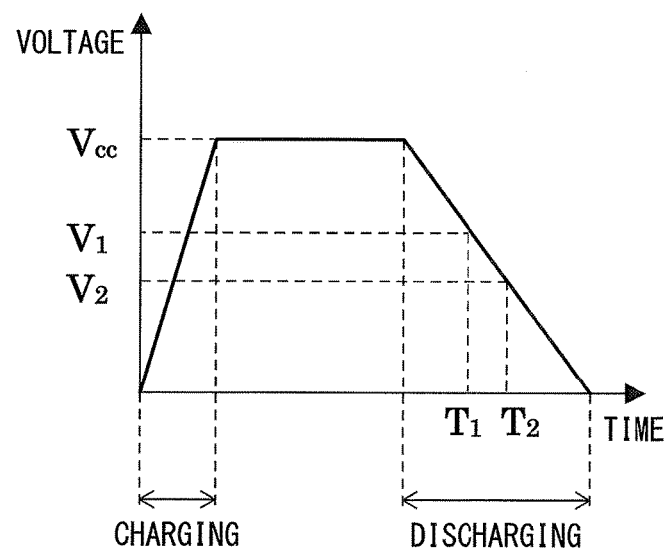
FIG. 5B is a graph showing a change in voltage over time during charging and discharging in the circuit shown in FIG. 5A by way of example.

FIG. 5B shows a graph which represents a change of voltage over time in the circuit illustrated in FIG. 5A by way of example. In the circuit shown in FIG. 5A, first, the contacts P1 and P2 are connected to each other to charge the desiccant 21. As a result, as shown in FIG. 5B, the voltage of the desiccant 21 increases to Vcc, which is maintained thereafter. Next, the contacts P1 and P3 are connected to discharge the current charged in the desiccant 21. After that, the current i flowing through the discharging circuit is measured from the voltage V1 applied to the fixed resistor 33 using the following equation (3).

$$i=V1/R1 \tag{3}$$

As can be seen in FIG. 5B, if the discharging time in which the voltage is decreased from V1 to V2 at a constant current i is (T2−T1), the electrostatic capacity Cx of the desiccant 21 can be obtained from the following equation (4).

$$Cx=i\times(T2-T1)/(V1-V2) \tag{4}$$

Figure 6:
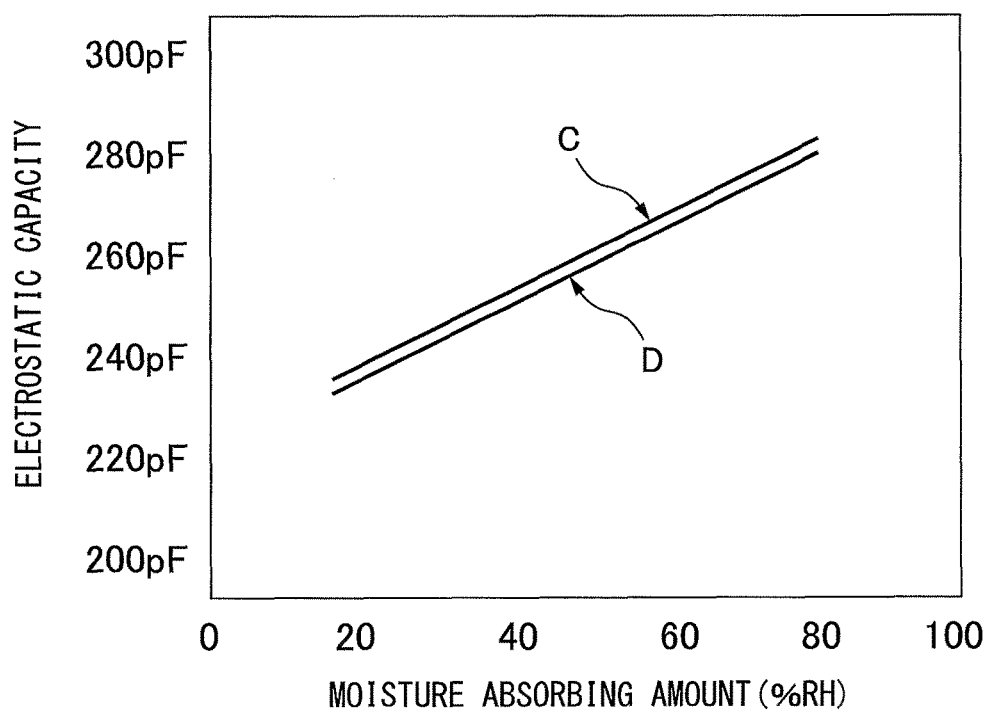
FIG. 6 is a graph showing the relationship between the moisture absorbing amount and the electrostatic capacity.

Moreover, FIG. 6 is a graph showing a relationship between the moisture absorbing amount and the electrostatic capacity. In FIG. 6, the curve C represents the case when the temperature is 25° C. and the curve D represents the case when the temperature is 60° C.

As may be understood from FIG. 6, the larger the moisture absorbing amount of the desiccant 21, the larger the dielectric constant, and accordingly, the larger the electrostatic capacity of the desiccant 21. Furthermore, the higher the temperature, the larger the absolute moisture amount in the air, and accordingly, the electrostatic capacity decreases as the temperature increases for the same moisture absorbing amount. As mentioned above, there is a correlation between the electrostatic capacity of the desiccant 21 and the moisture absorbing amount of the desiccant 21, and the straight line which represents the correlation between the moisture absorbing amount and the electrostatic capacity is shifted upward or downward depending on the temperature. Therefore, by measuring the electrostatic capacity of the desiccant 21 by the charging/discharging circuit shown in FIG. 5A and measuring the ambient temperature of the desiccant 21, it is possible to obtain the moisture absorbing amount of the desiccant 21 based on the correlation between the moisture absorbing amount and the electrostatic capacity as shown in FIG. 6. In this case, for example, it is preferable that correlative function between the moisture absorbing amount and the electrostatic capacity, including the temperature as a correction coefficient be obtained beforehand by experiments or simulation, etc., and be stored in the moisture absorbing amount calculation unit 28 shown in FIG. 2.

The following effects can be brought about by the rotary encoder discussed above.

In the rotary encoder 10 illustrated in FIG. 1, the components arranged on the flange 16, such as the rotary slit plate 15 or the light emitting element 19 are sealed by the cover member 23. Therefore, condensation may occur in the sealed space in the cover member 23 due to a sudden change of temperature or moisture or liquid may enter the sealed space of the cover member 23 through a structural gap of the rotary encoder 10, i.e., a gap between the bearing portion 11 and the rotating axis portion 13. Such condensation or intrusion of liquid may be a cause for damage to the rotary encoder 10, and accordingly, the desiccant 21 is arranged in the sealed space in the cover member 23. However, it is impossible to prevent the rotary encoder 10 from being damaged if condensation occurs or liquid enters, exceeding the moisture absorbing capacity of the desiccant 21. To this end, according to the present invention, by providing the function to acquire the moisture absorbing amount of the desiccant 21, not only can the occurrence of condensation or intrusion of liquid be detected but also the possibility that the amount of liquid increasing due to the condensation or the intruding liquid may be large enough not to be absorbed by the desiccant 21, can be predicted, whereby the rotary encoder can be prevented from being damaged. Furthermore, it is possible to reduce the maintenance time and enhance the operating rate of the motor by sending an alarm or a warning before the moisture absorbing amount exceeds the moisture absorbing capacity of the desiccant 21.

Note that, the damage to the rotary encoder 10 by liquid is exemplified as follows.

Namely, water droplets adhere to the electronic components or the light emitting element, etc., to which the drive signal is applied, a short-circuit easily occurs between the electrodes, resulting in critical damage to the electronic components or light emitting element, etc. Even if no drive voltage is applied to the electronic components or the light emitting element, if water droplets adhere to the internal components of the rotary encoder 10 due to condensation or intrusion of liquid, the components may be contaminated or corroded, thus leading to a remarkable decrease of the reliability thereof.

Second Embodiment

The second embodiment will be discussed below. In the following discussion, the same components as those in the first embodiment are assigned the same reference numerals and no explanation thereof will be given hereinafter. Only the difference from the components of the aforementioned first embodiment will be explained below.

Figure 7:
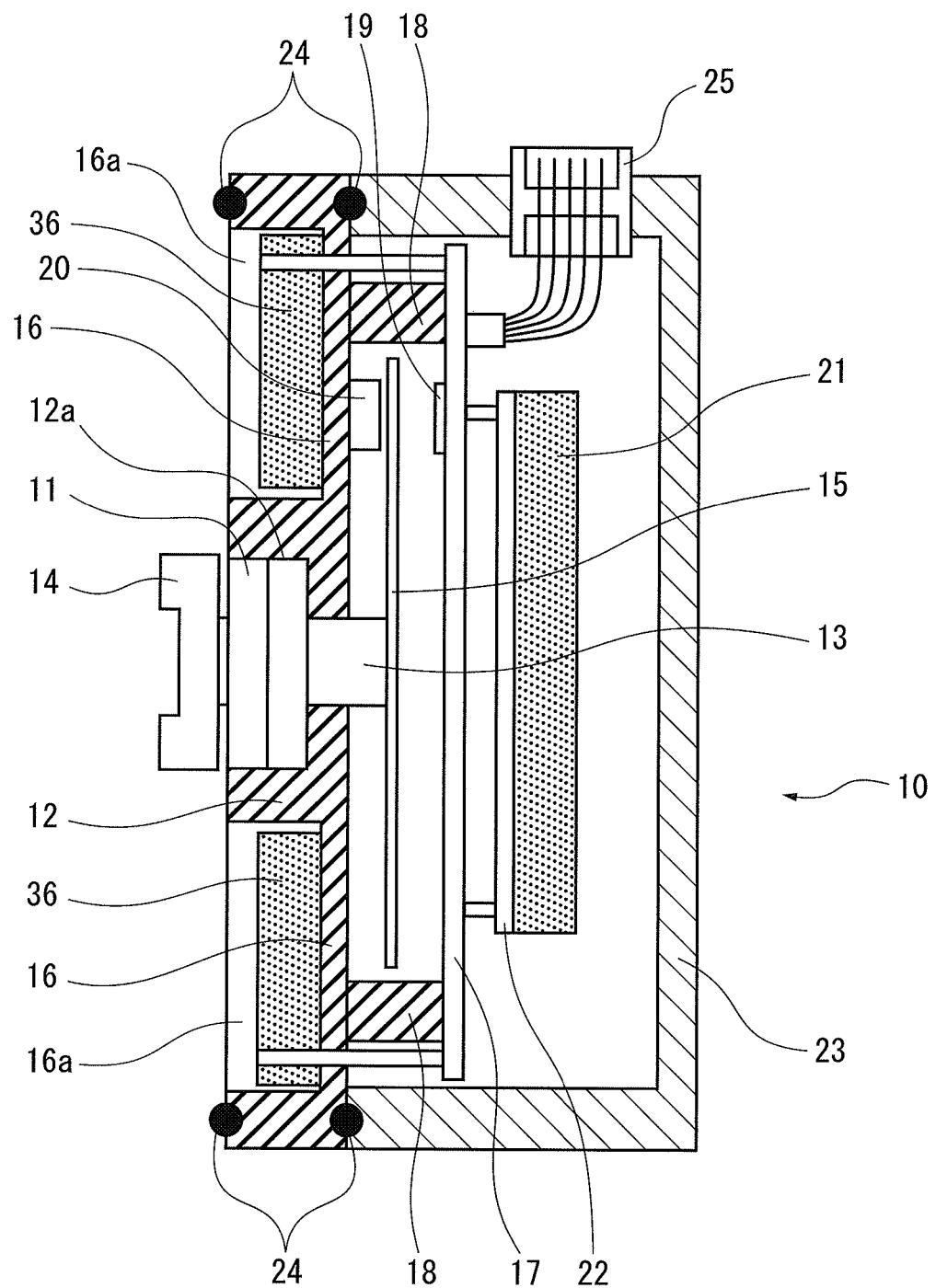
FIG. 7 is a schematic longitudinal sectional view of a rotary encoder according to a second embodiment of the present invention.

FIG. 7 schematically shows a longitudinal sectional view of the rotary encoder according to the second embodiment.

In the aforementioned first embodiment, the desiccant 21 is arranged in the sealed space in the cover member 23 and the electric circuit 17 for obtaining the moisture absorbing amount of the desiccant 21 is provided. However, in the present invention, the arrangement of the desiccant 21 is not limited to that shown in FIG. 1 in which the desiccant 21 is arranged on the holding member 22 in the cover member 23. In the second embodiment, as shown in FIG. 7, a desiccant 36 is additionally provided on the side of the flange 16 opposite to the cover member 23 and the moisture absorbing amount of the desiccant 36 is obtained by the electric circuit 17. The remaining structures of the second embodiment are the same as the first embodiment.

In the second embodiment, when the rotary encoder 10 is attached to the motor (servo motor), the rotating axis portion 13 of the rotary slit plate 15 is connected to a drive axis (not shown) of the motor through the joint 14 and the peripheral portion of the flange 16 abuts against the motor main body (not shown). The motor to which the rotary encoder 10 is attached uses a large amount of resin materials as an impregnant for the coil or an adhesive for the magnet and the moisture contained in the resin materials evaporates and turns to vapor due to heat generated by the motor. Therefore, the base member 12 of the rotary encoder 10 and the flange 16, opposed to the motor are exposed to the vapor. Moreover, as there is a spatial gap between the bearing portion 11 of the base member 12 and the rotating axis portion 13 of the rotary slit plate 15, the spatial gap forms a passage through which the vapor intrudes into the sealed space in the cover member 23.

Therefore, in the second embodiment, the additional desiccant 36 is arranged on the portion of the flange 16 that is opposed to the motor which generates vapor as shown in FIG. 7. Specifically, the flange 16 is provided with a recess 16a on the side of the flange opposite to the cover member 23. The recess 16a is hermetically sealed when the motor main body (not shown) abuts against the peripheral portion of the flange 16, so that the desiccant 36 is arranged in the recess 16a. The desiccant 36 arranged in the portion opposed to the motor makes it possible to reduce the possibility that vapor from the motor enters the sealed space in the cover member 23 through the gap between the bearing portion 11 of the base member 12 and the rotating axis portion 13 of the rotary slit plate 15. Note that, the number of the additional desiccants 36 is not limited to one, and the material of the desiccant is preferably the same as that of the desiccant 21 of the aforementioned first embodiment.

In the second embodiment, it is preferable that the electric circuit 17 has a function to obtain the moisture absorbing amount of the desiccant 36. The representative structure to obtain the moisture absorbing amount of the desiccant 36 is the same as that in the first embodiment.

According to the function to acquire the moisture absorbing amount of the desiccant 36, it is possible to quickly detect that the amount of moisture exceeding the moisture absorbing capacity of the desiccant 36 generated from the motor. Furthermore, it is possible to send an alarm or a warning signal to the outside of the rotary encoder 10 before the moisture enters the sealed space in the cover member 23.

Therefore, according to the second embodiment, it is possible to further reduce the occurrence of damage to the rotary encoder 10 by liquid, compared with the first embodiment.

Third Embodiment

Next, the third embodiment will be discussed below. In the following discussion, the same components as those in the first and second embodiments are assigned the same reference numerals and no explanation thereof will be given hereinafter. Only the difference from the components of the aforementioned first and second embodiments will be explained below.

Figure 8:
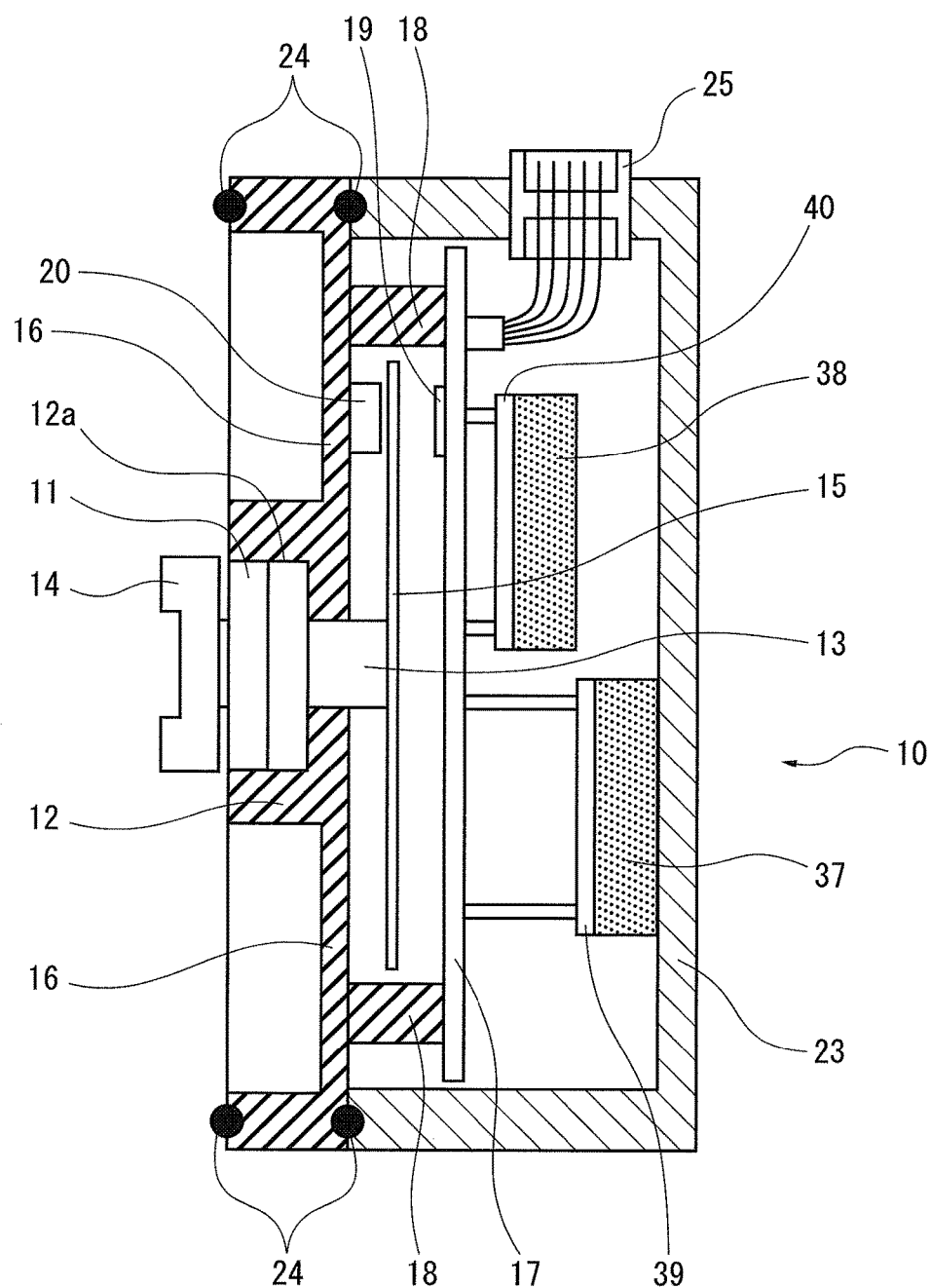
FIG. 8 is a schematic longitudinal sectional view of a rotary encoder according to a third embodiment of the present invention.

FIG. 8 schematically shows a longitudinal sectional view of the rotary encoder according to the third embodiment.

In the aforementioned first embodiment, the desiccant 21 is arranged in the sealed space in the cover member 23 and the electric circuit 17 for obtaining the moisture absorbing amount of the desiccant 21 is provided. In particular, in the first embodiment, as shown in FIG. 1, the desiccant 21 is not in contact with the components other than the holding member 22. However, in the sealed space defined by the flange 16 and the cover member 23, the cover member 23 which is directly in contact with the external air has the lowest temperature compared with the remaining components, and accordingly, it is most likely that condensation occurs first on the cover member 23.

In view of this, in the third embodiment, as shown in FIG. 8, a desiccant 37 and a holding member 39 which holds the desiccant 37 in contact with the cover member 23 are arranged in the sealed space in the cover member 23. With this arrangement of the desiccant 37, the condensation occurring on the cover member 23 can be quickly absorbed.

Furthermore, as shown in FIG. 8, a desiccant 38 which does not contact the cover member 23 and a holding member 40 which holds the desiccant 37 may be arranged in the sealed space in the cover member 23. Moreover, the number of the desiccants 37 and 38 is not limited to one and the material of the desiccants 37 and 38 are preferably the same as the material of the desiccant 21 in the first embodiment.

In the third embodiment, it is preferable that the electric circuit 17 has a function to obtain the moisture absorbing amounts of the desiccants 37 and 38. The representative structure to obtain the moisture absorbing amounts of the desiccants 37 and 38 is the same as that in the first embodiment. According to the function to acquire the moisture absorbing amounts of the desiccants 37 and 38, it is possible to prevent the moisture absorbing amounts of the desiccants 37 and 38 from exceeding the moisture absorbing capacities thereof. Furthermore, it is possible to send an alarm or a warning signal to the outside of the rotary encoder 10 to notify that the rotary encoder 10 may be damaged by the liquid before the moisture absorbing amounts exceed the respective moisture absorbing capacities.

In particular, according to the third embodiment, as the desiccant 37 is arranged in contact with the cover member 23 and the function to obtain the moisture absorbing amount of the desiccant 37 is provided, it is possible to detect the occurrence of a condensation in the sealed space in the cover member 23 in the early stage of the occurrence. Namely, according to the third embodiment, it is possible to recognize the occurrence of condensation in the rotary encoder, more speedily than the first embodiment.

Note that the rotary encoder 10 of the first to third embodiments is an optical rotary encoder, but the present invention is not limited to an optical rotary encoder. The present invention can be applied, for example, to a magnetic type or electric induction type rotary encoder. Moreover, the rotary encoder of the present invention is preferably applied as a feedback device for an NC machining tool or a servo motor provided in a robot. Furthermore, the rotary encoder of the present invention may be used integrally with or separately from the servo motor.

Although the above has been directed to representative embodiments, the present invention is not limited to the aforementioned embodiments and can be variously modified in shape, structure and material, etc., without departing from the spirit of the invention.

Effect of the Invention

According to the first aspect of the present invention, as the rotary encoder is provided with the electric circuit which obtains the moisture absorbing amount of the desiccant arranged in the hermetically sealed rotary encoder, it is possible to judge whether or not the desiccant has absorbed an amount of moisture close to the limit of the absorbing capacity, based on the acquired moisture absorbing amount.

Therefore, it is possible to send an alarm or a warning before the amount of liquid increasing due to condensation or intrusion of liquid in the rotary encoder exceeds the moisture absorbing capacity, to thereby prevent the rotary encoder from being damaged by liquid.

Furthermore, according to the first aspect, as the moisture absorbing amount of the desiccant can be obtained by the electric circuit that the rotary encoder itself possesses, it is not necessary to provide a separate moisture sensor or the like. Consequently, the rotary encoder can be miniaturized and the manufacturing cost thereof can be reduced.

According to the second aspect of the present invention, in the rotary encoder comprising a flange which is to be brought into contact with a motor, an additional desiccant is provided on the portion of the flange that is to be opposed to the motor, and the moisture absorbing amount of the additional desiccant is obtained as well. In the motor, for example, a large amount of resin material is used as an impregnant for the coil or as an adhesive for the magnet, and accordingly, the moisture contained in the resin material evaporates and turns into vapor due to heat of the motor. According to the second aspect, such a vapor from the motor can be absorbed by the desiccant to thereby reduce the possibility of intrusion of the moisture into the rotary encoder. Moreover, it is possible to speedily detect that an amount of moisture exceeding the moisture absorbing capacity of the desiccant has been generated from the motor. Furthermore, it is possible to send an alarm or a warning to the outside of the rotary encoder before such moisture enters the rotary encoder.

According to the third aspect of the present invention, as the desiccant is arranged in contact with the cover member in the sealed space in the cover member, it is possible to detect the occurrence of condensation in the sealed space in an early stage of the occurrence. Namely, as it is highly likely in the rotary encoder that condensation occurs first on the cover member which is in direct contact with the external air, the desiccant arranged on the cover member can quickly detect the occurrence of condensation in the rotary encoder.

According to the fourth aspect of the present invention, as there is a correlative relation between the electric resistance of the desiccant and the moisture absorbing amount thereof, it is possible to easily acquire the moisture absorbing amount of the desiccant by measuring the electric resistance of the desiccant.

According to the fifth aspect of the present invention, as there is a correlative relation between the electrostatic capacity of the desiccant and the moisture absorbing amount thereof, it is possible to easily acquire the moisture absorbing amount of the desiccant by measuring the electrostatic capacity of the desiccant.

According to the sixth aspect of the present invention, whether the desiccant has absorbed an amount of liquid close to the limit of the moisture absorbing capacity is judged based on the acquired moisture absorbing amount, and based on the judgment result, a signal can be outputted to notify that the desiccant will no longer be able to absorb a liquid.

What is claimed is:

1. A rotary encoder, comprising:
    a hermetically sealed structure configured to define a sealed space;
    a rotary plate arranged in the sealed space;
    at least one desiccant arranged in the sealed space;
    a circuit board arranged in the sealed space and including an electric circuit configured to obtain a moisture absorbing amount of the desiccant;
    an element provided on the circuit board for detection of rotation of the rotary plate; and
    a holding member attached to the circuit board and arranged in the sealed space, the holding member configured to hold the desiccant at a predetermined position in the sealed space.

2. The rotary encoder according to claim 1, further comprising a flange which is to be brought into contact with a motor,
    wherein at least one additional desiccant is arranged on the portion of the flange that is to be opposed to the motor,
    wherein the electric circuit is configured to obtain the moisture absorbing amount of the additional desiccant.

3. The rotary encoder according to claim 1, further comprising a flange which is to be brought into contact with a motor and a cover member which is attached to the flange and which defines the sealed space,
    wherein
    the at least one desiccant is arranged in contact with the cover member in the sealed space.

4. The rotary encoder according to claim 1, wherein
    the electric circuit comprises a measuring unit which measures an electrical resistance of each of the desiccants, and a moisture absorbing amount calculation unit which calculates the moisture absorbing amount of each desiccant, based on the measured electrical resistance.

5. The rotary encoder according to claim 1, wherein
    the electric circuit comprises a measuring unit which measures an electrostatic capacity of each of the desiccants, and a moisture absorbing amount calculation unit which calculates the moisture absorbing amount of each desiccant, based on the measured electrostatic capacity.

6. The rotary encoder according to claim 4, wherein
    the electric circuit further comprises a comparison judgment unit which judges whether or not the moisture absorbing amount calculated by the moisture absorbing amount calculation unit exceeds a predetermined threshold, and an output unit which outputs a signal to notify that each desiccant will be no longer able to absorb liquid if the calculated moisture absorbing amount exceeds the predetermined threshold.

* * * * *